United States Patent
Yuan et al.

(10) Patent No.: US 11,305,104 B2
(45) Date of Patent: Apr. 19, 2022

(54) SACCULAR CAVOPULMONARY ASSIST DEVICE

(71) Applicant: GUANGDONG CARDIOVASCULAR INSTITUTE, Guangdong (CN)

(72) Inventors: Haiyun Yuan, Guangdong (CN); Jian Zhuang, Guangdong (CN); Jimei Chen, Guangdong (CN); Chengbin Zhou, Guangdong (CN); Huanlei Huang, Guangdong (CN); Shusheng Wen, Guangdong (CN)

(73) Assignee: GUANGDONG CARDIOVASCULAR INSTITUTE, Guangdong (CN)

( * ) Notice: Subject to any disclaimer, the term of this patent is extended or adjusted under 35 U.S.C. 154(b) by 377 days.

(21) Appl. No.: 16/348,942

(22) PCT Filed: Mar. 29, 2018

(86) PCT No.: PCT/CN2018/080980
§ 371 (c)(1),
(2) Date: May 10, 2019

(87) PCT Pub. No.: WO2018/177342
PCT Pub. Date: Oct. 4, 2018

(65) Prior Publication Data
US 2020/0009305 A1 Jan. 9, 2020

(30) Foreign Application Priority Data
Mar. 31, 2017 (CN) .................. 201710204478.X

(51) Int. Cl.
*A61M 1/12* (2006.01)
*A61M 1/10* (2006.01)
(Continued)

(52) U.S. Cl.
CPC ........ *A61M 60/562* (2021.01); *A61M 60/857* (2021.01); *A61M 2205/02* (2013.01); *A61M 2210/125* (2013.01)

(58) Field of Classification Search
CPC .. A61M 60/148; A61M 60/43; A61M 60/268; A61M 60/50; A61M 60/894; A61M 60/898
See application file for complete search history.

(56) References Cited

U.S. PATENT DOCUMENTS

| 4,078,267 A | 3/1978 | Medyczna |
| 2003/0032854 A1 | 2/2003 | Palmer |

FOREIGN PATENT DOCUMENTS

| CN | 1093005 A | 10/1994 |
| CN | 201558364 U | 8/2010 |

(Continued)

OTHER PUBLICATIONS

International Search Report received in PCT/CN2018/080980, dated Jun. 21, 2018.
Office Action received in Chinese Patent Application No. 201710204478, dated Mar. 19, 2019.

*Primary Examiner* — Jon Eric C Morales
(74) *Attorney, Agent, or Firm* — Kilpatrick Townsend & Stockton LLP

(57) ABSTRACT

The present disclosure relates to a saccular cavopulmonary assist device, including a shell, an inflow tube (6) and an outflow tube (4), wherein a blood storage cavity (A) and a power cavity (B) are arranged in the shell, and the power cavity (B) is used for providing contraction and relaxation power for the blood storage cavity (A); the inflow tube (6) is arranged at a position corresponding to the power cavity (B) on the shell, an outer end is used for communicating with the vena cava, and an inner end communicates with the blood storage cavity (A) after passing through the power cavity (B); the outflow tube (4) is arranged at a position
(Continued)

corresponding to the blood storage cavity (A) on the shell, an outer end is used for communicating with the pulmonary artery, and an inner end communicates with the blood storage cavity (A). This device can assist the cavopulmonary circulation of the single ventricle, realize repeated blood drawing and pumping actions, provide the required power for the pulmonary circulation of the patient, and restore the biventricular blood flow in the human body; and because the arrangement of the inflow tube in the power cavity, the internal structure of this device is more compact, the overall shape is smaller, and the energy of the power cavity can be fully utilized.

19 Claims, 3 Drawing Sheets

(51) Int. Cl.
*A61M 60/562* (2021.01)
*A61M 60/857* (2021.01)

(56) References Cited

FOREIGN PATENT DOCUMENTS

| | | | | |
|---|---|---|---|---|
| CN | 201558367 U | 8/2010 | | |
| CN | 108653840 A | 10/2018 | | |
| WO | WO-2014115819 A1 | * | 7/2014 | .......... A61M 60/894 |
| WO | 2017009672 A1 | 1/2017 | | |
| WO | 2017027414 A1 | 2/2017 | | |

* cited by examiner

SACCULAR CAVOPULMONARY ASSIST DEVICE

The present application claims priority of Chinese application No. 201710204478.X, filed on Mar. 31, 2017. The disclosed content of the Chinese application is hereby entirely incorporated into the present disclosure.

FIELD OF THE DISCLOSURE

The present disclosure relates to the technical field of medical equipment, and in particular, to a saccular cavopulmonary assist device.

BACKGROUND OF THE DISCLOSURE

The Fontan operation and its modified procedures are often used for treating congenital heart disease of functional single ventricle and so on. With the progress of surgical and postoperative monitoring techniques, more and more patients with functional single ventricle survive to the adulthood. As patients' survival time prolonging, long-term complications of the Fontan circulation begin to appear, which greatly affects the quality of life of these patients, and leads to the failure of the Fontan circulation and transfers to heart transplantation.

To solve this problem, the prowered Fontan circulation is one of the solutions. To achieve the powered Fontan circulation, a cavopulmonary assist device is required. Among the related arts known to the inventors, the Berlin heart is a ventricle assist pump that is used relatively early in the world, the Luo-Ye pump is the first ventricle assist pump approved by the Chinese FDA for clinical use, but these pumps are especially designed for the left ventricle assistance and are not entirely suitable for the cavopulmonary assistance of the Fontan circulation. In addition, although the success of C-shaped pump and so forth can provide the basis for designing the cavopulmonary assist device of Fontan circulation, the above assist devices still need to be driven by external forces, which limit the clinical application and promotion of such devices.

SUMMARY OF THE DISCLOSURE

The present disclosure provides a saccular cavopulmonary assist device, which can provide direct power for the pulmonary circulation and restore biventricular blood flow in the body.

A first aspect of the embodiment of the present disclosure provides a saccular cavopulmonary assist device, including:

a shell with a blood storage cavity and a power cavity separate from each other, and the power cavity is used for providing contraction and relaxation power for the blood storage cavity;

an inflow tube arranged at a position corresponding to the power cavity on the shell, wherein an outer end of the inflow tube is used for communicating with a vena cava, and an inner end of the inflow tube communicates with the blood storage cavity after passing through the power cavity; and an outflow tube arranged at a position corresponding to the blood storage cavity on the shell, wherein an outer end of the outflow tube is used for communicating with the pulmonary artery, and an inner end of the outflow tube communicates with the blood storage cavity.

In some embodiments, the saccular cavopulmonary assist device further includes an inner membrane arranged in the shell to divide the inner space of the shell into the blood storage cavity and the power cavity, and the inner end of the inflow tube communicates with the blood storage cavity after successively passing through the power cavity and the inner membrane.

In some embodiments, the shell includes a first shell and a second shell buckled with each other, and the inner membrane is arranged at the boundary of the first shell and the second shell, the blood storage cavity is formed between the first shell and the inner membrane, and the power cavity is formed between the second shell and the inner membrane.

In some embodiments, the saccular cavopulmonary assist device further includes a connecting tube arranged at a position corresponding to the power cavity on the shell, and the two ends of the connecting tube are respectively connected with the power cavity and a component capable of providing self-power in a human body.

In some embodiments, the power cavity is configured to be connected with an aorta cavity through the connecting tube, and a flexible first diaphragm is provided at one end of the connecting tube away from the power cavity to separate an inner cavity of the connecting tube from the aorta cavity, so as to transfer the pressure change of the aorta to the power cavity.

In some embodiments, the first diaphragm is of an elliptical structure and is configured to be connected to a side wall of the aorta, and one end of the connecting tube away from the power cavity expands outward to connect with the first diaphragm.

In some embodiments, the power cavity is configured to connected with a ventricle cavity at the pulmonary valve annulus through the connecting tube, and a flexible second diaphragm is provided at one end of the connecting tube away from the power cavity to separate the inner cavity of the connecting tube from the ventricle cavity, so as to transfer a systolic pressure and a diastolic pressure of the ventricle cavity to the power cavity.

In some embodiments, the second diaphragm is of a saccular structure, the saccular structure passes through the pulmonary valve annulus and stretches into the ventricle cavity, and one end of the connecting tube away from the power cavity is connected with an opening of the saccular structure.

In some embodiments, the saccular cavopulmonary assist device further includes an anti-reflux structure for allowing the blood to flow from the inflow tube to the blood storage cavity in a one-way manner.

In some embodiments, the anti-reflux structure is arranged at a communication site of the inflow tube and the blood storage cavity.

In some embodiments, the saccular cavopulmonary assist device further includes an inner membrane arranged in the shell to divide the inner space of the shell into the blood storage cavity and the power cavity;

wherein the anti-reflux structure includes a diaphragm, one end of the diaphragm is connected with a partial circumference of the inner end of the inflow tube, and the other end of the diaphragm is free and the inflow tube passes through the inner membrane, so that the outlet of the inflow tube is formed between the diaphragm and the inner membrane.

In some embodiments, the outer contour of the diaphragm adjacent to the edge of the inner membrane is matched with the outer contour of the inner membrane.

In some embodiments, the inner membrane is provided with an opening, and the inner end of the inflow tube passes through the opening, and the outer wall of the inner end of the inflow tube forms a sealed connection with the edge of the opening.

In some embodiments, the opening is a gap, the length of the gap corresponds to the circumferential size of the inner end of the inflow tube, and the outer walls of the upper and lower parts of the inner end of the inflow tube are respectively adhered with two opposite surfaces of the gap after being expanded by the inflow tube.

In some embodiments, a part of the inflow tube in the shell and the diaphragm are made of a flexible material.

In some embodiments, the inflow tube and the diaphragm are integrally formed.

In some embodiments, the saccular cavopulmonary assist device further includes a supporting tube arranged at a position corresponding to the inflow tube on the shell, and the inflow tube is partially arranged in the supporting tube.

In some embodiments, the blood storage cavity is a hemispherical-like cavity, and the power cavity is a cylindrical-like cavity.

In some embodiments, the inner wall of the first shell is coated with a coating comprising an anticoagulant substance.

According to the saccular cavopulmonary assist device provided by the present disclosure, the inflow tube and the outflow tube are respectively arranged at the positions corresponding to the power cavity and the blood storage cavity on the shell, the outer end of the inflow tube is used for communicating with the vena cava, the inner end of the inflow tube communicates with the blood storage cavity after passing through the power cavity, the outer end of the outflow tube is used for communicating with the pulmonary artery, and the inner end of the outflow communicates with the blood storage cavity. Such circulation device can assist the cavopulmonary circulation of the single ventricle, pump in and pump out the blood repeatedly, and provide the required power for the pulmonary circulation to make the blood flow close to normal in the patient body; and because the arrangement of the inflow tube occupies the space inside the power cavity, the internal stmcture of the circulation device is more compact, the overall volume is smaller, and the power of the power cavity can be fully utilized.

BRIEF DESCRIPTION OF THE ACCOMPANYING DRAWINGS

The drawings described herein are used for providing a further understanding of the present disclosure, and constitute a part of the present application. The illustrative embodiments of the present disclosure and the descriptions thereof are used for explaining the present disclosure and do not constitute improper limitation to the present disclosure. In the drawings.

DETAILED DESCRIPTION OF THE PREFERRED EMBODIMENTS

The present disclosure is described in detail below. In the following paragraphs, different aspects of the embodiments are defined in more detail. Various aspects so defined may be combined with any other one or more aspects unless clearly indicated that they are not combinable. In particular, any feature that is considered to be preferred or advantageous may be combined with other one or more features that are considered to be preferred or advantageous.

The terms "first", "second" and the like appearing in the present disclosure are merely for the convenience of description to distinguish different components having the same name, and do not indicate sequential or primary and secondary relations.

In the description of the present disclosure, it should be understood that the orientational or positional relations indicated by the terms "length", "width", "height", "upper", "lower", "left", and "right" and the like are orientational or positional relations based on the drawings, are merely for the convenience of the description of the present disclosure, and are not intended to indicate or imply that the device must have a particular orientation, must be constructed and operated in a particular orientation, and thus cannot be construed as limitations to the protection scope of the present disclosure.

The success of the Fontan operation suggests that single ventricle can drive the blood circulation of the whole body of the patient, but is less effective. At present, there is no self-powered cavopulmonary assist device which can make full use of the single ventricular kinetic energy and improve the efficiency of driving pulmonary circulation, which is conductive to the long-term survival of such patients and the clinical application of these devices.

Figure 1:
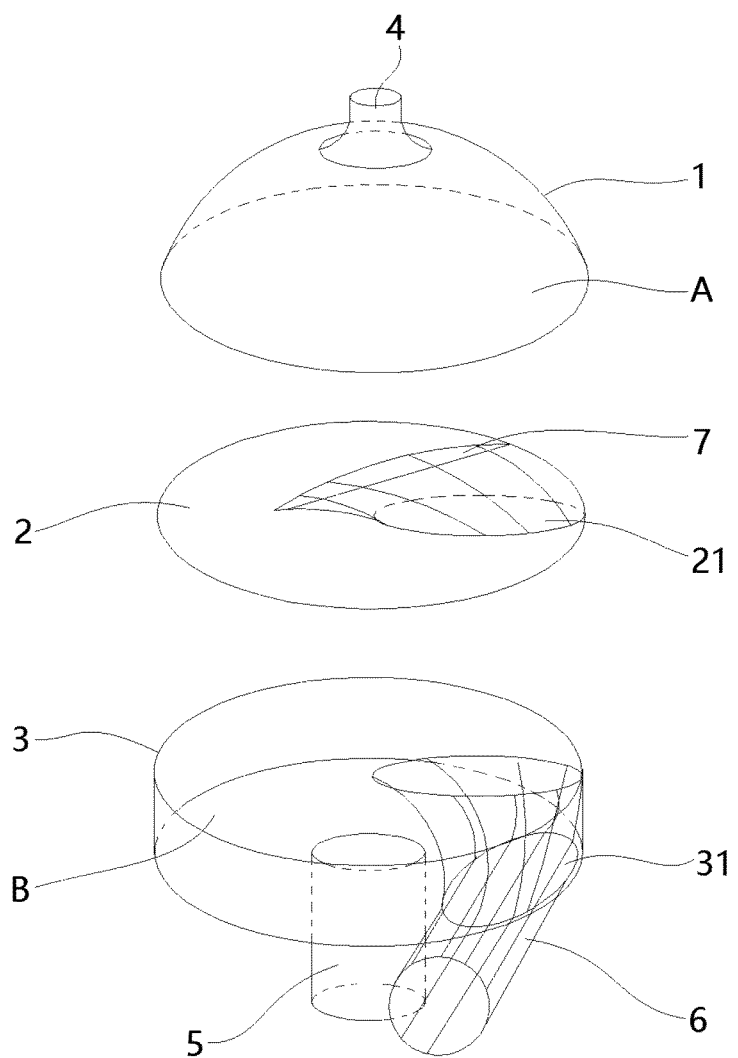
FIG. 1 is an exploded schematic diagram of an embodiment of a saccular cavopulmonary assist device of the present disclosure.
Figure 2:
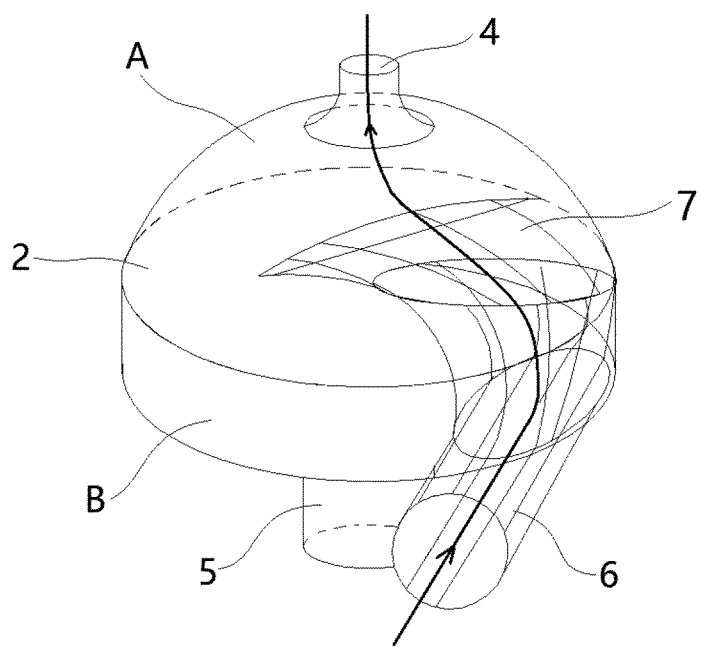
FIG. 2 is a schematic diagram of an external stmcture of an embodiment of a saccular cavopulmonary assist device of the present disclosure.

As shown in FIGS. 1 and 2, the present disclosure provides a saccular cavopulmonary assist device (hereinafter referred to as "assist device"). In some embodiments, the assist device includes a shell, an inflow tube 6 and an outflow tube 4, wherein the shell is provided with a blood storage cavity A and a power cavity B separate from each other, the power cavity B is used for providing contraction and relaxation power for the blood storage cavity A. In some embodiments, the power cavity B can be filled with normal saline or other fluid. When the pressure in the power cavity B decreases, the blood storage cavity A relaxes, and the assist device draws the blood; and when the pressure in the power cavity B rises, the blood storage cavity A contracts, and the assist device pumps out the blood.

The inflow tube 6 is arranged on a part of the shell defining the power cavity B, the outer end of the inflow tube 6 is used for communicating with a vena cava, and the inner end of the inflow tube 6 communicates with the blood storage cavity A after passing through the power cavity B. The outflow tube 4 is arranged on a part of the shell defining the blood storage cavity A, the outer end of the outflow tube 4 is used for communicating with a pulmonary artery, and the inner end of the outflow tube 4 communicates with the blood storage cavity A.

The blood drawing and pumping actions are mainly realized in the blood storage cavity A, when the power cavity B provides the power for the relaxation of the blood storage cavity A, the blood in the vena cava flows into the blood storage cavity A through the inflow tube 6, and the assist device is in a blood drawing state. When the power cavity B provides the power for the contraction of the blood storage cavity A, the blood in the blood storage cavity A is pumped out into the pulmonary artery through the outflow tube 4, and the assist device is in a blood pumping state.

The illustrative embodiment has at least one of the following advantages:

(1) Such assist device can achieve blood drawing and pumping actions repeatedly, and can provide power and pulsating blood flow for the pulmonary circulation of a single ventricle patient. The assist device draws the blood when the heart of the human body relaxes, and pumps the blood when the heart of the human body contracts. The effect of the assist device is similar to that of the normal heart of the human body, and make the patient recover the biventricular blood flow.

(2) Since the arrangement of the inflow tube occupies the space of the power cavity, the layout of the assist device is more compact, the overall volume is smaller, and the kinetic energy of the power cavity can be fully utilized Compared with the structure in which the inflow tube and the outflow tube are respectively arranged at both ends of the blood storage cavity, the space occupied by the assist device in the horizontal direction can also be reduced.

(3) Since the inflow tube and the outflow tube are respectively arranged on the shell corresponding to the two independent cavities, the blood naturally forms a circuitous path when flowing to prevent the occurrence of thrombus. Compared with the structure in which the inflow tube and the outflow tube are respectively arranged at both ends of the blood storage cavity, the circuitous path can be formed during the flowing of the blood without increasing the lengths of the inflow tube and the outflow tube, and the resistance is only produced in the inflow tube when blood flows, so the resistance coefficient can be reduced when the blood flows to reduce the energy loss when the assist device is at work.

(4) No additional valve is needed to reduce the damage to the blood cells. The complicated external power and control systems are reduced by using the self-power of the single ventricle, the energy efficiency is improved, and the balance of systemic circulation and pulmonary circulation is promoted, which is conducive to the long-term survival of the patients.

In order to form the blood storage cavity A and the power cavity B, in some embodiments, the assist device can further include an inner membrane 2, the inner membrane 2 is arranged in the shell, the outer edge of the inner membrane can be connected to the shell and divides the inner space of the shell into the blood storage cavity A and the power cavity B, the inner end of the inflow tube 6 communicates with the blood storage cavity A after successively passing through the power cavity B and the inner membrane 2.

The inner membrane 2 can be made of a flexible material, or can be made of an autologous pericardium or a material with similar effects, so that when the pressure in the power cavity B rises or decreases, the blood storage cavity A can contract or relax through the deformation of the inner membrane 2. As the inner membrane 2 is made of the material exemplified herein, the energy consumption in the working process of the assist device can be reduced, and the volume of the assist device can be reduced when the equivalent function is required.

An opening 21 is formed in the inner membrane 2, and the inner end of the inflow tube 6 communicates with the blood storage cavity A after passing through the opening 21. In order to ensure the independence between the blood storage cavity A and the power cavity B, the outer wall of the inner end (i.e., the outlet of the inflow tube 6) of the inflow tube 6 forms a sealed connection with the edge of the opening 21 to prevent blood in the blood storage cavity A from flowing into the power cavity B.

The opening 21 can be designed into a shape matched with the outer wall of the inflow tube 6, for example, the opening 21 is elliptical, the opening 21 allows the inner end of the inflow tube 6 to pass through in a free state; or the opening 21 includes a gap and needs to be expanded to allow the inner end of the inflow tube 6 to pass through, and the length of the gap corresponds to the circumferential size of the inner end of the inflow tube 6, and the outer walls of the upper and lower parts of the inner end of the inflow tube 6 are respectively adhered with two opposite surfaces of the gap after being expanded by the inflow tube 6.

In some embodiments, the opening 21 is arranged at a position staggered with the outflow tube 4 on the inner membrane 2, in this way, the flow path of the blood in the blood storage cavity A can be further prolonged to reduce the possibility of thrombus formation and ensure smoother blood flow.

For a specific structure, as shown in FIG. 1, the shell includes a first shell 1 and a second shell 3 which are buckled with each other, and the inner membrane 2 is arranged at the boundary of the first shell 1 and the second shell 3, the blood storage cavity A is formed between the first shell 1 and the inner membrane 2, the power cavity B is formed between the second shell 3 and the inner membrane 2, and the split shell is adopted to provide convenience for the installation of the inner membrane 2 and the inflow tube 6.

Correspondingly, the inflow tube 6 can be arranged on the second shell 3. The outflow tube 4 can be arranged on the first shell 1. In some embodiments, the outflow tube 4 is located at the top or a position close to the top of the blood storage cavity A, which meets the blood fluid dynamics, such that blood can flow out easily.

In some embodiments, the inner wall of the first shell 3 is coated with a coating, and the coating can adopt a lining heparin coating or other anticoagulant substance, so that the flow of the blood is smoother.

In some embodiments, the first shell 1 is a hemispherical-like shell, and the second shell 3 is a cylindrical-like shell having an open end, such that the blood storage cavity A forms a hemispherical-like cavity, and the power cavity B forms a cylindrical-like cavity, and the cavity in such shape has better hemodynamics Correspondingly, the inner membrane 2 is circular. For example, the first shell 1 is a hemispherical shell, and the second shell 3 is a cylindrical shell having an open end, so that the blood storage cavity A forms a hemispherical cavity, and the power cavity B forms a cylindrical cavity.

In addition, those skilled in the art can also design the blood storage cavity A and the power cavity B into other shapes according to the requirements of the fluid mechanics, for example, the power cavity B is also a hemispherical-like cavity, and the cavity of any shape must have better haemodynamics effect.

On this basis, as shown in FIG. 1, the assist device of the present disclosure further includes a connecting tube 5, the connecting tube 5 is arranged at a position corresponding to the power cavity B on the shell, for example, the connecting tube 5 is arranged on the second shell 3, and the two ends of the connecting tube 5 are respectively connected with the power cavity B and a component capable of providing power in the human body. Such assist device can omit the external force driving, and use the ventricle power of the patient to drive the blood storage cavity A to achieve blood drawing and pumping actions. For the assist device in which the second shell 3 is the cylindrical shell having the open end, the connecting tube 5 can be arranged at the end of the second shell 3 along the axis.

In some embodiments, one end of the connecting tube 5 away from the power cavity B is provided with a flexible diaphragm for separating an inner cavity of the connecting tube 5 from the cavity of the component capable of providing power in the human body, so as to transfer the self-power of the patient to the power cavity B.

Figure 5:
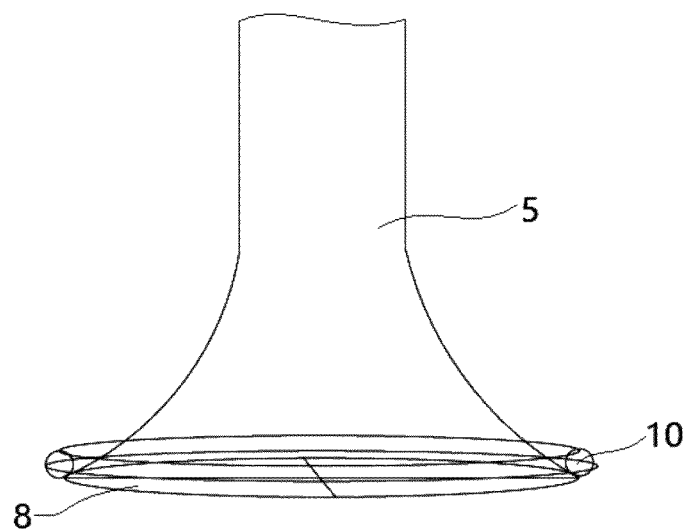
FIG. 5 is a schematic diagram of a connection structure of an embodiment in which the power cavity in the saccular cavopulmonary assist device of the present disclosure is connected with an aorta cavity.

When the patient is subjected to surgery, if the aorta structure of the patient is good, referring to FIG. 5, the power cavity B is connected with the aorta cavity through the connecting tube 5, and the diaphragm is a flexible first diaphragm 8 arranged at one end of the connecting tube 5 away from the power cavity B, and the first diaphragm 8 closes the end of the connecting tube 5 away from the power cavity B for separating the inner cavity of the connecting tube 5 from the aorta cavity. The ventricle contraction and relaxation of the patient can cause a pressure change in the aorta, so that the first diaphragm 8 deforms to transfer the pressure change in the aorta to the power cavity B.

In some embodiments, as shown in FIG. 5, the first diaphragm 8 is of an elliptical structure, the first diaphragm 8 can be fixed on the side wall of the aorta by suturing or the like, one end of the connecting tube 5 away from the power cavity B expands outward to connect with the elliptical first diaphragm 8. Because the aorta is of a round tube structure, the elliptical first diaphragm 8 is beneficially sutured on the side wall of the aorta. During the suturing, the long axis of the elliptical first diaphragm 8 can be parallel to the long axis of the aorta. The end of the connecting tube 5 away from the power cavity B expands outward along the long axis of the first diaphragm 8 mainly for conforming with the side wall of the aorta, which is conducive to transferring the pressure in the aorta cavity to the power cavity B.

Further, such an assist device further includes a connecting ring 10 arranged at a connection site of the connecting tube 5 and the first diaphragm 8, which is used for assisting to suture the connecting tube 5 on the side wall of the aorta, and making the connection between the connecting tube 5 and the first diaphragm 8 be more reliable. The connecting ring 10 can be made of a non-degradable biomaterial.

When the structure shown in FIG. 5 is adopted, the power transmission mode is: during the ventricle contraction and relaxation of the patient, the aorta pressure changes, and the first diaphragm 8 becomes convex or concave to transfer the pressure change of the aorta to the power cavity B.

Figure 6:
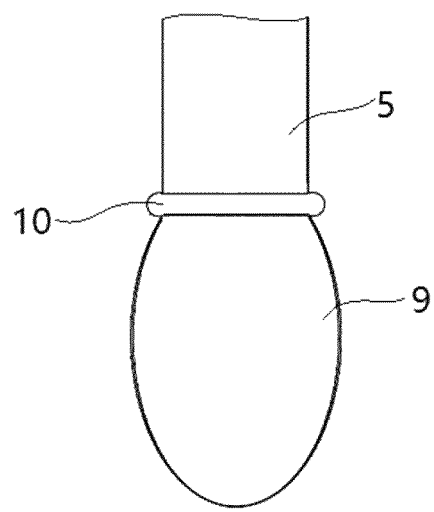
FIG. 6 is a schematic diagram of a connection structure of an embodiment in which the power cavity in the saccular cavopulmonary assist device of the present disclosure is connected with a ventricle cavity.

When the patient is subjected to surgery, if the pulmonary valve annulus of the patient is well developed, referring to FIG. 6, the power cavity B is connected with the ventricle cavity at the pulmonary valve annulus through the connecting tube 5, the diaphragm is a flexible second diaphragm 9 arranged at one end of the connecting tube 5 away from the power cavity B, and the second diaphragm 9 closes one end of the connecting tube 5 away from the power cavity B for separating the inner cavity of the connecting tube 5 from the ventricle cavity. The ventricle contraction and relaxation of the patient can cause a pressure change in the ventricle cavity, causing the second diaphragm 9 to deform to transfer the systolic pressure and the diastolic pressure of the ventricle cavity to the power cavity B.

In some embodiments, as shown in FIG. 6, the second diaphragm 9 is of a saccular structure, the saccular structure passes through the pulmonary valve annulus and stretches into the ventricle cavity, and one end of the connecting tube 5 away from the power cavity B is connected with an opening of the saccular structure. The second diaphragm 9 can be fixed on the pulmonary valve annulus by suturing or the like.

In the structural form of FIG. 6, the second membrane is of the saccular structure. Of course, the shape of the saccular structure can also be other irregular shapes matching the shape of the ventricle cavity.

When the structural form shown in FIG. 6 is adopted, the power transmission mode is: the ventricle contraction and relaxation of the patient can cause the pressure change in the ventricle cavity, so that the second diaphragm 9 deforms to change the volume of the saccular structure so as to transfer the systolic pressure and the diastolic pressure of the ventricle cavity to the power cavity B.

The present disclosure can make full use of the function of each ventricle muscle in the heart by making the saccular structure pass through the pulmonary valve annulus and stretch into the ventricle cavity, and the flexible saccular structure can shrink when the intraventricular pressure rises, so that the inner wall of the saccular structure can be flushed and the formation of thrombosis can be reduced.

Further, such assist device can further include a connecting ring 10, the connecting ring 10 is arranged at a connection site of the connecting tube 5 and the second diaphragm 9, for example, the connecting ring 10 is arranged the connection site of the connecting tube 5 and the opening of the saccular structure, which is used for assisting to suture the connecting tube 5 on the pulmonary valve annulus, and making the connection between the connecting tube 5 and the second diaphragm 9 be more reliable. The connecting ring 10 can be made of a non-degradable biomaterial.

On the basis of the above embodiments, the assist device of the present disclosure further includes an anti-reflux structure for allowing the blood to flow from the inflow tube 6 into the blood storage cavity A in a one-way manner and preventing the blood from reversely flowing from the blood storage cavity A to the inflow tube 6, which is similar to a one-way structure.

In some embodiments, as shown in FIGS. 1 and 2, the anti-reflux structure is arranged at the communication site between the inflow tube 6 and the blood storage cavity A, that is, at the inner end of the inflow tube 6 or at a position close to the inner membrane 2, and similarly a ureter to bladder segment structure is adopted. The anti-reflux structure is easily provided at the position of the inflow tube 6, the anti-reflux structure is easily formed integrally with the inflow tube 6, and the inner membrane 2 can be used for assisting the work of the anti-reflux structure. In other embodiments, the anti-reflux structure can also be arranged at any location in the inflow tube 6.

Specifically, the anti-reflux structure includes a diaphragm 7, one end of the diaphragm 7 is connected with a partial circumference of the inner end of the inflow tube 6, and the other end of the diaphragm 7 is free, that is a flaky structure extending out from the outlet position of the inflow tube 6. After the inflow tube 6 passes through the inner membrane 2, the outlet of the inflow tube 6 is located between the diaphragm 7 and the inner membrane 2, that is, the diaphragm 7 and the inner membrane 2 are arranged up and down oppositely.

This anti-reflux structure reduces the need for an additional artificial anti-reflux valve, the blood flows into the blood storage cavity A after flowing out from the inner end of the inflow tube 6, and the diaphragm 7 can not increase the resistance to the flow of the blood. The arrangement of the anti-reflux structure basically does not increase the drag coefficient when the blood flows.

In some embodiments, as shown in FIG. 2, the outer contour of the membrane 7 adjacent to the edge of the inner membrane 2 is matched with the shape of the outer contour of the inner membrane 2. For example, for a circular inner membrane 2, the outer contour of the membrane 7 adjacent to the edge of the inner membrane 2 has the same curvature as the inner membrane 2. The diaphragm 7 of this shape can further reduce the resistance coefficient when the blood flows.

Preferably, the inflow tube 6 and the diaphragm 7 are integrally formed, thereby being convenient to manufacture. Alternatively, the inflow tube 6 and the diaphragm 7 can also be separately molded and then joined together.

In order to open and close the outlet of the inflow tube 6, in some embodiments, the part of the inflow tube 6 located in the shell and the diaphragm 7 are made of a flexible material. Thus, when the pressure in the power cavity B changes, the side wall of the inflow tube 6 is easily deformed with the movement of the inner membrane 2 to open and close the outlet of the inflow tube 6. At the same time, when the anti-reflux structure is opened, when the blood flows out from the outlet of the inflow tube 6 and flows into the blood storage cavity A, the flexible diaphragm 7 can be opened, and the diaphragm 7 is preferably made of an anti-adhesion material; and when the anti-reflux structure is closed, the inflow tube 6 is in a squashed state, the outlet of the inflow tube 6 is closed, and the flexible diaphragm 7 can also be closely fitted to the inner membrane 2 to further resist the reflux of the blood.

With respect to the embodiment in which the inflow tube 6 is made of the flexible material, the position of the inflow tube 6 needs to be maintained. As shown in FIG. 1, the assist device of the present disclosure further includes a supporting tube, the supporting tube is arranged at a position corresponding to the inflow tube 6 on the shell, for example, the supporting tube is arranged at a position corresponding to the inflow tube 6 on the second shell 3, and the inflow tube 6 is partially arranged in the supporting tube.

Specifically, for the cylindrical-like second shell 3, one end of the supporting tube is arranged on the sidewall of the second shell 3 and forms an open pore 31, and the other end is free and located at the outside of the second shell 3. The supporting tube can be separately fixed on the second shell 3 or integrally formed with the shell. The inflow tube 6 is penetrated in the supporting tube to provide a support for a part of length segment of the flexible inflow tube 6, so as to locate the inflow tube 6 at a suitable position, and meanwhile support and protect the inflow tube 6, thereby avoiding the inflow tube 6 being damaged by the external force to prolong the service life of the assist device.

In a specific structural form, the opening 21 formed in the inner membrane 2 is a gap, and the gap is arranged along the radial direction and located on one side of a circle center of the inner membrane 2, and the length of the gap corresponds to the circumferential size of the inner end of the inflow tube 6. After the inner end of the inflow tube 6 passes through the gap, the gap is expanded, the inner edge size of the expanded gap is matched with the circumferential size of the inner end of the inflow tube 6, so that the inner membrane 2 is in close fit with the inflow tube 6 at the gap, thereby improving the sealing property and preventing the blood from permeating into the power cavity B from the blood storage cavity A.

Further, in order to improve the firmness and the sealing property of the connection between the inner membrane 2 and the inflow tube 6, the outer walls of the upper and lower parts of the inner end of the inflow tube 6 are respectively adhered with two opposite surfaces after the gap is expanded by the inflow tube 6, so that the inner membrane 2 is fixed integrally with the inflow tube 6, and the deformation of the inner membrane 2 makes the side wall of the inflow tube 6 move in order to open and close the outlet of the inflow tube 6.

In order that those skilled in the art can understand the working principle of the assist device as shown in FIG. 1 more clearly, a detailed description will be given below with reference to the state diagrams shown in FIG. 3 and FIG. 4.

Figure 3:
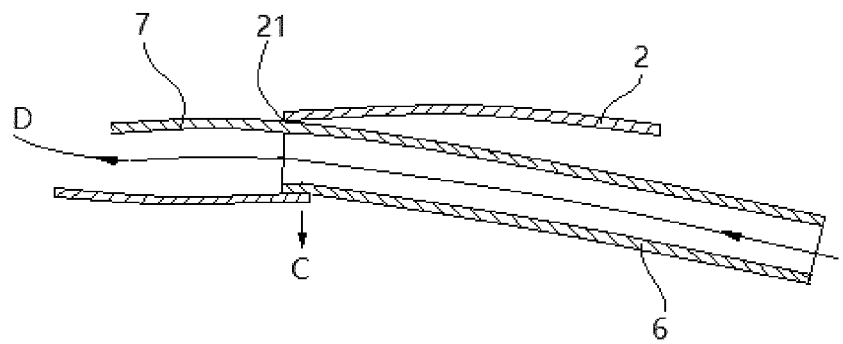
FIG. 3 is a structural schematic diagram when an antireflux structure in the saccular cavopulmonary assist device of the present disclosure is open.

As shown in FIG. 3, when the pressure of the power cavity B decreases, the inner membrane 2 is curved toward the power cavity B (downward along an arrow C), and the volume of the blood storage cavity A becomes larger. At the same time, the inner membrane 2 drives the part of the inner end of the inflow tube 6 connected with the inner membrane 2 to move, so that the inner end of the inflow tube 6 is expanded, and meanwhile, the inner membrane 2 is separated from the diaphragm 7. At this time, the anti-reflux structure is in the open state, which connects the passage of the blood from the inflow tube 6 to the blood storage cavity A, the blood in the vena cava flows into the blood storage cavity A through the inflow tube 6 along an arrow D, and the assist device is in a blood drawing state.

Figure 4:
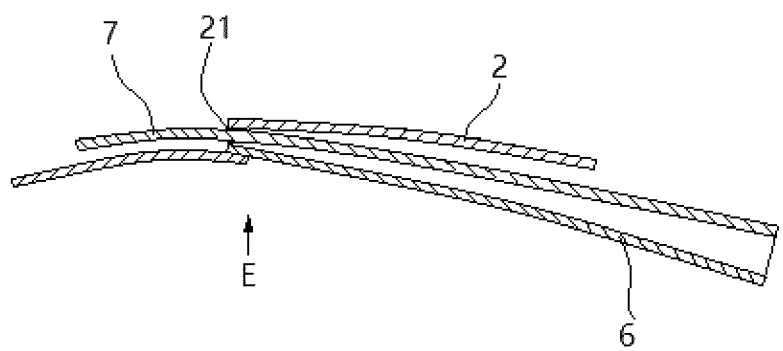
FIG. 4 is a structural schematic diagram when the antireflux structure in the saccular cavopulmonary assist device of the present disclosure is closed.

As shown in FIG. 4, when the pressure of the power cavity B rises, the inner membrane 2 is curved toward the blood storage cavity A (upward along an arrow E), and the volume of the blood storage cavity A becomes smaller. At the same time, the inner membrane 2 drives a part of the inner end of the inflow tube 6 connected with the inner membrane 2 to move, so that the inner end of the inflow tube 6 is squashed, and the inner membrane 2 is fitted to the diaphragm 7. At this time, the anti-reflux structure is in the closed state to close the passage of the blood from the inflow tube 6 to the blood storage cavity A, the blood in the blood storage cavity A is pumped out into the pulmonary artery through the outflow tube 4, the blood in the blood storage cavity A generates no reflux, and the assist device is in a blood pumping state.

The assist device of the present disclosure is designed to solve the problem of the pulmonary circulation power of the Fontan circulation, and can simulate the pulsating power provided by the right ventricle to the pulmonary circulation without increasing an anti-reflux valve. Different from the device designed to improve the insufficient power of the left ventricle, the assist device adopts the self-power of a single ventricle, thus reducing the complicated power and control systems, realizing the balance of the systemic circulation and the pulmonary circulation more easily and laying a foundation for the ultimate realization of the powered Fontan circulation.

Compared with the traditional Fontan circulation, the powered Fontan circulation avoids ventricle muscle atrophy caused by the ligation of the pulmonary artery, and can preserve and utilize the contractile function of all myocardia in a single ventricle to the greatest extent. In addition, no artificial mechanical valve needs to be added in the assist device, so that the damage to the blood components is small. In summary, the assistive device can improve the efficiency of the single ventricle as a whole and greatly improve the surgical treatment effects and long-term prognosis of patients with a single ventricle.

The assist device assist device of the present disclosure can be fabricated by using an artificial biomaterial having better histocompatibility and a heparin inner coating, for example, an integrated assist device is fabricated in by using a 3D printing method. Or, the assist device can also be fabricated by using a conventional mold and using the same material as the Luo-Ye pump or the like in the prior art. Or, stem cells can be used for growing a biopump on the backbone of the pump. The fabricated assist device can be experimentally verified in vitro or in vivo to ensure the effectiveness and safety of the assist device in use.

The saccular cavopulmonary assist device provided by the present disclosure has been described in detail above. The principles and embodiments of the present disclosure have been described with reference to the specific embodiments herein, and the description of the above embodiments is only used for helping to understand the method of the present disclosure and its core idea. It should be noted that those of ordinary skill in the art can make a number of improvements and modifications to the present disclosure without departing from the principles of the present disclosure, and these modifications and modifications shall also fall within the protection scope of the present disclosure.

The invention claimed is:

1. A saccular cavopulmonary assist device, comprising:
a shell with a blood storage cavity (A) and a power cavity (B) separate from each other, and the power cavity (B) is configured to provide contraction and relaxation power for the blood storage cavity (A);
an inflow tube (6) arranged on a part of the shell defining the power cavity (B), wherein an outer end of the inflow tube (6) is configured to communicate with a vena cava, and an inner end of the inflow tube (6) communicates with the blood storage cavity (A) after passing through the power cavity (B); and
an outflow tube (4) arranged on a part of the shell defining the blood storage cavity (A), wherein an outer end of the outflow tube (4) is configured to communicate with a pulmonary artery, and an inner end of the outflow tube (4) communicates with the blood storage cavity (A).

2. The saccular cavopulmonary assist device according to claim 1, further comprising an inner membrane (2) arranged in the shell, to divide an inner space of the shell into the blood storage cavity (A) and the power cavity (B), and the inner end of the inflow tube (6) communicates with the blood storage cavity (A) after successively passing through the power cavity (B) and the inner membrane (2).

3. The saccular cavopulmonary assist device according to claim 2, wherein the shell comprises a first shell (1) and a second shell (3) buckled with each other, and the inner membrane (2) is arranged at a boundary of the first shell (1) and the second shell (3), the blood storage cavity (A) is formed between the first shell (1) and the inner membrane (2), and the power cavity (B) is formed between the second shell (3) and the inner membrane (2).

4. The saccular cavopulmonary assist device according to claim 3, wherein an inner wall of the first shell (1) is coated with a coating comprising an anticoagulant substance.

5. The saccular cavopulmonary assist device according to claim 2, wherein the inner membrane (2) is provided with an opening (21), and an inner end of the inflow tube (6) passes through the opening (21), and an outer wall of the inner end of the inflow tube (6) forms a sealed connection with an edge of the opening (21).

6. The saccular cavopulmonary assist device according to claim 5, wherein the opening (21) comprises a gap, a length of the gap corresponds to a circumferential size of the inner end of the inflow tube (6), and outer walls of upper and lower parts of the inner end of the inflow tube (6) are respectively adhered with two opposite surfaces of the gap after being expanded by the inflow tube (6).

7. The saccular cavopulmonary assist device according to claim 1, further comprising a connecting tube (5) arranged at a position corresponding to the power cavity (B) on the shell, and the two ends of the connecting tube (5) are respectively connected with the power cavity (B) and a component capable of providing power in a human body.

8. The saccular cavopulmonary assist device according to claim 7, wherein the power cavity (B) is configured to be connected with an aorta cavity through the connecting tube (5), and a flexible first diaphragm (8) is provided at one end of the connecting tube (5) away from the power cavity (B) to separate an inner cavity of the connecting tube (5) from the aorta cavity, so as to transfer a pressure change of the aorta to the power cavity (B).

9. The saccular cavopulmonary assist device according to claim 8, wherein the first diaphragm (8) is of an elliptical structure and configured to be connected to a side wall of the aorta, and one end of the connecting tube (5) away from the power cavity (B) expands outward to connect with the first diaphragm (8).

10. The saccular cavopulmonary assist device according to claim 7, wherein the power cavity (B) is configured to connected with a ventricle cavity at a pulmonary valve annulus through the connecting tube (5), and a flexible second diaphragm (9) is provided at one end of the connecting tube (5) away from the power cavity (B) to separate the inner cavity of the connecting tube (5) from the ventricle cavity, so as to transfer a systolic pressure and a diastolic pressure of the ventricle cavity to the power cavity (B).

11. The saccular cavopulmonary assist device according to claim 10, wherein the second diaphragm (9) is of a saccular structure, the saccular structure passes through the pulmonary valve annulus and stretches into the ventricle cavity, and one end of the connecting tube (5) away from the power cavity (B) is connected with an opening of the saccular structure.

12. The saccular cavopulmonary assist device according to claim 1, further comprising an anti-reflux structure configured to allow the blood to flow from the inflow tube (6) to the blood storage cavity (A) in a one-way manner.

13. The saccular cavopulmonary assist device according to claim 12, wherein the anti-reflux structure is arranged at a communication site of the inflow tube (6) and the blood storage cavity (A).

14. The saccular cavopulmonary assist device according to claim 12, further comprising an inner membrane (2) arranged in the shell to divide an inner space of the shell into the blood storage cavity (A) and the power cavity (B);
wherein the anti-reflux structure comprises a diaphragm (7), one end of the diaphragm (7) is connected with a partial circumference of the inner end of the inflow tube (6), and the other end of the diaphragm (7) is free, and the inflow tube (6) passes through the inner membrane (2) so that an outlet of the inflow tube (6) is formed between the diaphragm (7) and the inner membrane (2).

15. The saccular cavopulmonary assist device according to claim 14, wherein an outer contour of the diaphragm (7) adjacent to an edge of the inner membrane (2) is matched with the outer contour of the inner membrane (2).

16. The saccular cavopulmonary assist device according to claim 14, wherein a part of the inflow tube (6) in the shell and the diaphragm (7) are made of a flexible material.

17. The saccular cavopulmonary assist device according to claim 14, wherein the inflow tube (6) and the diaphragm (7) are integrally formed.

18. The saccular cavopulmonary assist device according to claim 1, further comprising a supporting tube arranged at a position corresponding to the inflow tube (6) on the shell, wherein the inflow tube (6) is partially arranged in the supporting tube.

19. The saccular cavopulmonary assist device according to claim 1, wherein the blood storage cavity (A) is a hemispherical-like cavity, and the power cavity (B) is a cylindrical-like cavity.

* * * * *